United States Patent [19]

Hirsch et al.

[11] Patent Number: 5,895,373
[45] Date of Patent: Apr. 20, 1999

[54] FEEDING TUBE RETAINING MEMBER FILLING TOOL

[75] Inventors: William H. Hirsch, Gahanna; Donald J. Goldhardt, Grove City, both of Ohio

[73] Assignee: Abbott Laboratories, Abbott Park, Ill.

[21] Appl. No.: 08/729,612

[22] Filed: Oct. 11, 1996

[51] Int. Cl.$^6$ ................................. A61M 29/00
[52] U.S. Cl. .................... 604/97; 604/96; 604/104; 606/196
[58] Field of Search ...................... 604/28, 49, 54, 604/96–109, 181, 146, 152; 606/191–198

[56] References Cited

U.S. PATENT DOCUMENTS

| | | | |
|---|---|---|---|
| 3,352,531 | 11/1967 | Kilmarx | 604/99 |
| 3,385,301 | 5/1968 | Harautuneian | 604/99 |
| 3,399,677 | 9/1968 | Gould et al. | 604/99 |
| 3,409,015 | 11/1968 | Swanson | 604/99 |
| 4,207,891 | 6/1980 | Bolduc | 604/97 |
| 4,495,948 | 1/1985 | Shapiro | 604/99 |
| 4,655,749 | 4/1987 | Fischione | 606/192 |
| 4,758,223 | 7/1988 | Rydell | 604/98 |
| 5,545,133 | 8/1996 | Burns et al. | 604/96 |
| 5,647,847 | 7/1997 | Lafontaine et al. | 604/97 |
| 5,695,468 | 12/1997 | Lafontaine et al. | 604/99 |

*Primary Examiner*—Ronald Stright
*Attorney, Agent, or Firm*—Brian R. Woodworth; Daniel J. Hulseberg

[57] ABSTRACT

A method for placing an external feeding tube in the gastro intestinal tract of a patient. The device includes a feeding tube and a filling tool for filling a fillable retaining member of a feeding tube. The tool includes a fluid reservoir constructed to contain a fluid therein. The tool further includes a tool body defining a fluid flow path, the tool body constructed to be connected to the fluid reservoir such that the fluid reservoir is in fluid communication with the fluid flow path defined by the tool body. The filling tool further includes a cannula constructed to connect fluidly to a filling lumen of a feeding tube. The cannula is fluidly connected to the fluid flow path.

6 Claims, 3 Drawing Sheets

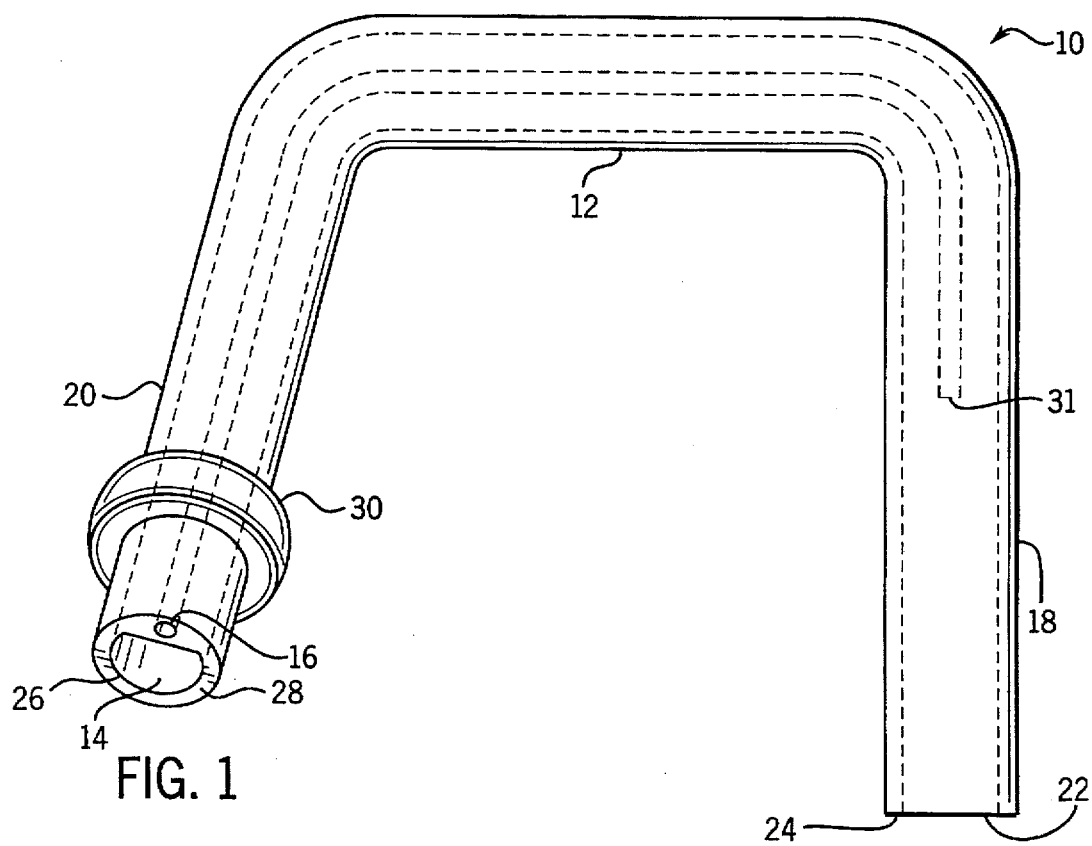
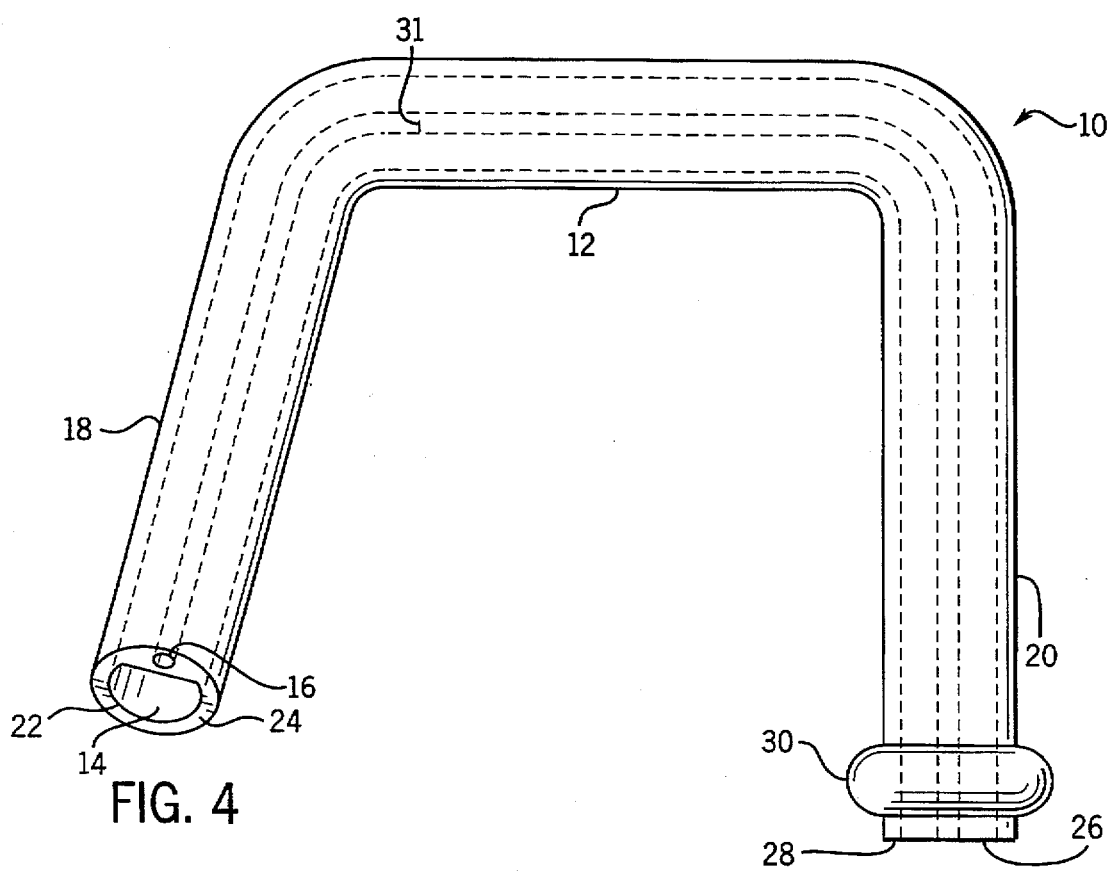

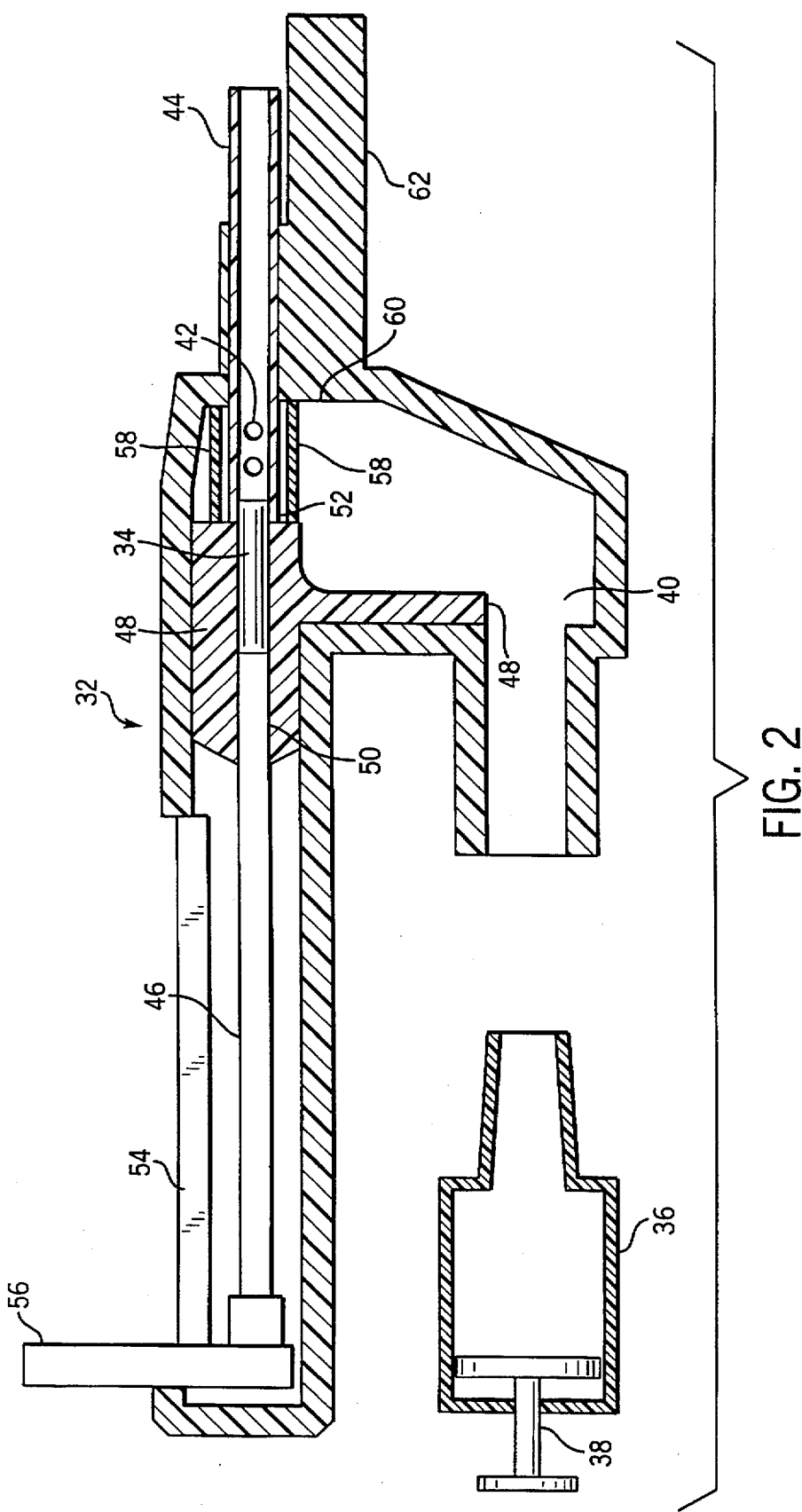

FEEDING TUBE RETAINING MEMBER FILLING TOOL

TECHNICAL FIELD

This invention relates to an apparatus for filling an expandable retaining member of a feeding tube.

BACKGROUND OF THE INVENTION

Gastrostomy and jejunostomy tubes are used to deliver nutritional products to the gastrointestinal tract of a patient. Gastrostomy tubes are positioned such that a nutritional product is delivered percutaneously from an external source directly to the patient's stomach. Jejunostomy tubes are positioned such that the nutritional product is delivered to the patient's small bowel. Gastrostomy and jejunostomy tubes are referred to collectively herein as "feeding tubes."

In one method for placing a feeding tube in a patient, an endoscope is passed down the patient's esophagus in order to view the esophagus and to ensure that there are no obstructions or lesions in the esophagus that will inhibit or preclude the passage of the tube through the esophagus. The endoscope also may be used to examine the interior of the stomach and/or the small bowel to select an entry point for the feeding tube. Next, the doctor transilluminates the entry point by directing light outwardly from endoscope such that the light shines through the patient's abdominal wall, thereby identifying the location at which the feeding tube is to enter the gastrointestinal tract. The doctor then makes an incision through the abdominal wall into the gastrointestinal tract and passes a first end of a guidewire percutaneously into the stomach through the resulting incision. Alternatively, the doctor may insert a hollow needle through the abdominal wall and into the stomach, and then pass a first end of a guidewire percutaneously into the stomach through the hollow needle. The first end of the guidewire is grasped with a grasping tool which may be associated with the endoscope, and the grasping tool and the guidewire are drawn outwardly from the patient's stomach and esophagus and through the patient's mouth. Upon completing this step of the procedure, a second end of the guidewire remains external to the patient's abdominal wall while the first end of the guidewire extends through the patient's mouth.

In one technique for feeding tube placement, the first end of the guidewire is attached to a feeding tube. By pulling on the second end of the guidewire, the feeding tube is pulled through the patient's mouth and esophagus, and then into the stomach. Further pulling of the second end of the guidewire causes the feeding tube to exit the stomach through the abdominal wall. Passage of the feeding tube through the abdominal wall may be facilitated by placing a dilating, conical tip on the leading end of the feeding tube. The feeding tube then is pulled through the abdominal wall until a retaining member mounted on the second end of the feeding tube engages the interior of the stomach. This technique is referred to as a "pull" technique.

In an alternative technique for feeding tube placement, the feeding tube is placed over the guidewire and is pushed along the guidewire such that the feeding tube passes through the patient's mouth, esophagus, and stomach until the first end of the feeding tube exits through the abdominal wall. The feeding tube is then drawn through abdominal wall until the retaining member on the second end of the feeding tube engages the interior of the stomach. This technique is referred to as a "push" or an "over-the-wire" technique.

Feeding tubes also can be placed by inserting the feeding tube through a stoma tract formed through the patient's abdominal wall. Insertion of the internal end of the feeding tube typically is facilitated by using dilators in order to provide an adequate tract through which the feeding tube and the retaining member can be inserted. This technique is preferably used to place feeding tubes through mature stoma tracts, but may be used when tumors or lesions within the patient's esophagus preclude passage of the feeding tube through the esophagus.

A variety of retaining members are used to prevent the feeding tube from exiting through the patient's abdominal wall after it has been placed. For example, a variety of shapes of fillable "balloon" retaining members are commercially available. These retaining members are fluidly connected to a filling channel. The filling channel can be formed integrally with the feeding tube, i.e., formed within or on an exterior surface of the feeding tube, or can be a separate element. The filling channel extends to a position outside of the patient and typically terminates at a valve. In order to fill the retaining member, a fluid, e.g., air, water, glycerine, or saline, is injected through the valve and into the retaining member. In order to empty the retaining member, the fluid is withdrawn from the retaining member via the valve. A syringe typically is used in order to fill and empty the retaining member.

The valve associated with known fillable retaining members is readily accessible at a point exterior to the patient. As a result of the accessibility of these valves, there is a possibility of an inadvertent release of pressure from the retaining member, thus making it possible to inadvertently remove the feeding tube from the patient. In addition, due to the accessibility of the valve, medical professionals sometimes overutilize the valve, resulting in the overfilling, and in some cases the bursting, of the fillable retaining member.

Fillable retaining members are typically constructed of silicone or latex rubber which tends to degrade in the presence of gastric juices over relatively extended periods of time. In addition, it has been found that silicone retaining members, when filled with water, may lose volume over time due to hydraulic and osmotic pressures across the wall of the retaining member.

SUMMARY OF THE INVENTION

The present invention is directed to a filling tool. The filling tool includes a tool body that defines a fluid flow path therethrough. The tool body is constructed for fluid connection with a fluid reservoir. The fluid flow path is fluidly connected to a cannula which is constructed to connect fluidly to a filling lumen of a feeding tube. In the preferred embodiment of the filling tool of the present invention, a plunger is associated with the fluid reservoir in order to permit fluid to be forced from or drawn into the fluid reservoir of the tool. The tool further includes a plug injector configured to force a plug outwardly from the tool body, through the cannula, and into the filling lumen of the feeding tube such that the plug is positioned at a point spaced from the external end of the filling lumen.

BRIEF DESCRIPTION OF THE DRAWINGS

In the accompanying drawings that form part of the specification, and in which like numerals are employed to designate like parts throughout the same:

FIG. 1 is an elevational view of a feeding tube that can be used with the tool of the present invention;

FIG. 2 is a cross-sectional view of a filling tool constructed in accordance with the preferred embodiment of the present invention;

FIG. 4 is an elevational view of view of an alternative embodiment of a feeding tube that can be used with the tool of the present invention.

DESCRIPTION OF THE PREFERRED EMBODIMENT

Figure 3:
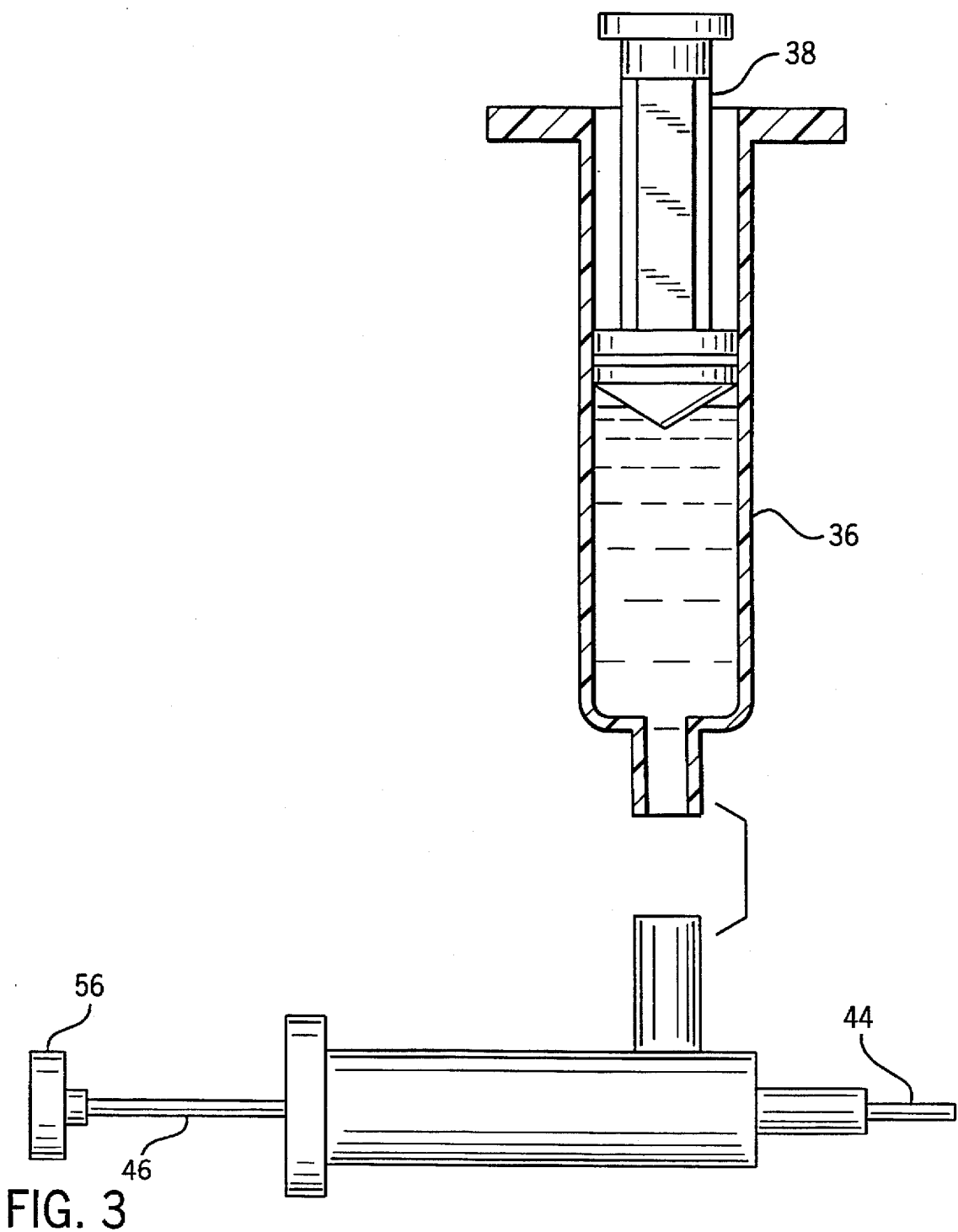
FIG. 3 is an elevational view of a first alternative embodiment of the filling tool of the present invention.

While this invention is susceptible of embodiment in many different forms, this specification and the accompanying drawings disclose only one specific form as an example of the invention. The invention is not intended to be limited to the embodiment so described. The scope of the invention is pointed out in the appended claims.

For ease of description, the apparatus of this invention is described in the normal (upright) operating position, and terms such as upper, lower, horizontal, etc., are used with reference to this position. It will be understood, however, that the apparatus of this invention may be manufactured, stored, transported, and sold in an orientation other than the position described.

The figures illustrating the apparatus show some elements that are known and that will be recognized by one skilled in the art. The detailed descriptions of such elements are not necessary to an understanding of the invention, and accordingly, are herein presented only to the degree necessary to facilitate an understanding of the novel features of the present invention.

The apparatus of this invention is used with certain conventional components the details of which, although not fully illustrated or described, will be apparent to those having skill in the art and an understanding of the necessary functions of such components.

A feeding tube apparatus is generally indicated at 10 in FIG. 1. Apparatus 10 is constructed of biocompatible materials and includes a feeding tube 12. Feeding tube 12 defines feeding lumen 14 and filling lumen 16 therethrough. In the embodiment depicted in FIG. 1, feeding lumen 14 has a substantially D-shaped cross-section and filling lumen 16 is disposed proximal the flat interior edge of feeding lumen 14. In this embodiment, filling lumen 16 is circular or elliptical cross-section. In the depicted embodiment, feeding tube 12 has a substantially circular external configuration. However, it is to be appreciated that the present invention is not limited to feeding tube devices having a D-shaped feeding lumen or a circular or elliptical filling lumen as depicted in FIG. 1. For example, feeding tube 12 can be constructed such that both feeding lumen 14 and filling lumen 16 are substantially polygonal in cross-section. Feeding tube 12 also can be constructed such that it has a polygonal external configuration. In addition, feeding tube 12 can be constructed such that filling lumen 16 is attached to an exterior surface of feeding tube 12. Feeding tube 12 also can be constructed such that filling lumen 16 is entirely separate therefrom.

Feeding tube 12 includes an external end portion 18 and an internal end portion 20. In the embodiment of the present invention depicted in FIG. 1, feeding tube portion 12 defines inlet feeding aperture 22 therethrough at external terminal end 24. Inlet feeding aperture 22 is configured to permit a nutritional product to be introduced into feeding lumen 14 from an external source. For example, feeding aperture 22 can be configured to receive therein an adaptor constructed to connect fluidly to a conduit which in turn can be fluidly connected to a source of an enteral nutritional product. Feeding aperture 22 also can be configured to connect directly to a source of an enteral nutritional product or to a conduit that is fluidly connected to a source of an enteral nutritional product. Feeding tube 12 also defines outlet feeding aperture 26 therethrough at internal terminal end 28. Outlet feeding aperture 26 is configured to permit an enteral nutritional product to flow from feeding lumen 14 into a patient's stomach or small intestine. Although inlet feeding aperture 22 and outlet feeding aperture 26 are positioned at the terminal ends of feeding tube portion 12 of the embodiment of the tube depicted in FIG. 1, it will be appreciated that they can be positioned at any point along external end portion 18 and internal end portion 20, respectively, without departing from the spirit and scope of the present invention.

Retaining member 30 is mounted on internal end portion 20 of feeding tube 12. Retaining member 30 is configured to engage the interior surface of the stomach or small intestine as feeding tube 12 is urged outwardly, thereby preventing inadvertent removal of feeding tube 12 from the patient through a stoma tract formed through the patient's abdominal wall. Retaining member 30 can be positioned at any point along internal end portion 20, the precise position being determined by the needs of the patient and the preferences of the doctor. Retaining member 30 of the preferred embodiment of the feeding tube depicted herein is a fillable member, the interior of which is in fluid communication with filling lumen 16 of feeding tube portion 12. Retaining member 30 can have a variety of shapes without departing from the scope of the present invention.

Retaining member 30 can be constructed of an expandable, biocompatible material such as silicone. However, it is preferable that retaining member 30 be constructed of a polyurethane material in order to provide better functional characteristics. Due to the relative strengths of polyurethane and silicone, a polyurethane retaining member can be constructed from an extruded material that is significantly thinner than the material used to fabricate a silicone retaining member. Polyurethane also is less susceptible than silicone to degradation resulting from exposure to gastric juices, thereby allowing the polyurethane retaining member to be used over a longer period of time.

Retaining member 30 is preferably a preformed, fillable body. The term "preformed" implies that the walls of the body are not significantly stretched as the body is filled to a predetermined volume, i.e., its initial capacity. Thus, the outer diameter of retaining member 30 is greater than the outer diameter of feeding tube portion 12 both when retaining member 30 is empty and when it is filled to its initial capacity. When retaining member 30 is filled, the individual introducing fluid into the retaining member will feel little or no resistance until the initial capacity of the retaining member is reached. In order to fill the retaining member beyond the initial capacity, the individual will have to apply a force to the fluid that is great enough to stretch the walls of the retaining member. This resistant force will be readily noticed by the individual, thereby providing a signal that the retaining member has reached its initial capacity. As a result, the individual will know when to stop adding fluid to the retaining member, thereby decreasing or eliminating the possibility of overfilling and/or bursting the retaining member. In addition, because the walls of the retaining member are not under substantial stress, i.e., not substantially stretched, when the retaining member is filled to its initial capacity, the retaining member of the present invention will be less susceptible to structural failure during use. Further, because the walls of the retaining member are not under substantial stress when the retaining member is filled to its initial capacity, the hydraulic pressure gradient across the wall of retaining member 30 does not pose a significant leakage problem.

In the embodiment of feeding tube 12 depicted in FIG. 1, filling lumen 16 extends from internal terminal end 28 to retaining member 30 and from retaining member 30 to a point 31 on the external end portion side of retaining member 30. In the depicted embodiment, filling lumen 16 is fluidly sealed at point 31. Point 31 is selected such that it is external to the patient when apparatus 10 of the present invention is in use. The precise location of point 31 preferably is selected to fit the size of the patient and the desires of the doctor. In the embodiment of the invention depicted in FIG. 1, filling lumen 16 terminates at point 31.

Feeding tube 12 can have a variety of configurations without departing from the spirit and scope of the present invention. For example, in a first alternative configuration of feeding tube 12, filling lumen 16 extends from internal terminal end 28 to retaining member 30 and from retaining member 30 to external terminal end 24, as depicted in FIG. 4. In the first alternative configuration, a substantially fluid-tight seal is provided at point 31. In the configurations of the feeding tube of the present invention depicted in FIGS. 1 and 4, filling lumen 16 and retaining member 30 can be accessed only from the internal end portion side of retaining member 30.

In a second alternative configuration of feeding tube 12 not depicted herein, filling lumen 16 also is open to an external environment of feeding tube 12 at external terminal end 24 or at another point on external end portion 18. In this configuration of the feeding tube, fluid can be introduced into filling lumen 16 and retaining member 30 from external end portion 18. In the second alternative configuration, filling lumen 16 can terminate at retaining member 30 or can be fluidly sealed at a point on the interior end portion side of retaining member 30. In the alternative, filling lumen 16 may extend from retaining member 30 to internal terminal end 28. It will be appreciated that a seal such as a plug must be provided in filling lumen 16 on each side of retaining member 30 that is open to an external environment. This will be discussed in greater detail herein.

In order to empty retaining member 30 from the external end portion side of retaining member 30 in the first and second configurations of feeding tube 12, it is necessary to sever filling lumen 16 at a point between point 31 and retaining member 30, thereby allowing fluid to drain from retaining member 30. In order to enable an individual to identify the position of point 31, indicia can be provided on feeding tube 12.

The present invention is directed to a filling tool generally indicated at 32 in FIG. 2. Filling tool 32 is constructed to force fluid through filling lumen 16 and into retaining member 30 in order to fill retaining member 30. Filling tool 32 of the present invention also is constructed to force plug 34 into filling lumen 16 following the filling of retaining member 30. Plug 34 is configured to provide a substantially fluid tight seal of filling lumen 16 when positioned therein. In the preferred embodiment of the present invention, plug 34 is substantially cylindrical and has an outer diameter that is not less than the inner diameter of filling lumen 16. However, it will be appreciated that the size and configuration of plug 34 will vary dependent upon the configuration of feeding tube 12 and filling lumen 16 formed therethrough.

Filling tool 32 can be constructed of a variety of materials. In the preferred embodiment, filling tool 32 is constructed of a plastic material, thereby reducing the cost of manufacture of filling tool 32. Filling tool 32 of the preferred embodiment of the present invention is an inexpensive, single-use device when constructed of plastic.

Filling tool 32 includes fluid reservoir 36 which is constructed to contain a fluid used to fill retaining member 30. The particular fluid used can be a gas, e.g., air, or a liquid, e.g., glycerine, water, or saline. Fluid reservoir 36 can be a permanently attached element of filling tool 32. However, in the preferred embodiment of the present invention depicted in FIG. 2, fluid reservoir 36 is releasably attachable to filling tool 32, e.g., by way of a luer or a locking luer connection. In the preferred embodiment, plunger 38 of known construction and operation is provided to force fluid out of or to draw fluid into fluid reservoir 36. In this embodiment, fluid reservoir 36 and plunger 38 can be in the form of a commercially available syringe having a luer or locking luer configuration for fluid connection with filling tool 32. It will be appreciated by those of ordinary skill in the art that other known mechanisms can be used in lieu of plunger 38 without departing from the spirit and scope of the present invention. For example, filling tool 32 or fluid reservoir 36 can be provided with a pump of known construction that is configured to force fluid out of or into fluid reservoir 36. Fluid reservoir 36 also can be configured such that it can be squeezed to force fluid therefrom into retaining member 30. For example, fluid reservoir 36 can be a bellows-like container having a luer or locking luer connection. In addition, it will be appreciated that fluid can be forced from fluid reservoir 36 into retaining member 30 or from retaining member 30 to fluid reservoir 36 by adjusting the vertical position of fluid reservoir 36 relative to the vertical position of retaining member 30.

In the preferred embodiment of the present invention depicted in FIG. 2, fluid reservoir 36 is configured such that plunger 38 is pushed in a plane substantially parallel to the plane of filling lumen 16 when filling lumen is connected to filling tool 32. In the alternative embodiment of the present invention depicted in FIG. 3, plunger 38 is pushed in a plane substantially perpendicular to the plane of filling lumen 16. It is believed that the preferred embodiment of the present invention depicted in FIG. 2 offers better ergonomic performance characteristics than the embodiment of the present invention depicted in FIG. 3. However, it will be appreciated that the direction of movement of plunger 38 required to force fluid from fluid reservoir 36 can be varied without departing from the scope of the present invention claimed herein.

In the embodiment of the present invention depicted in FIG. 2, fluid reservoir 36 is fluidly connectable to fluid flow channel 40 defined by filling tool 32. As above-discussed, fluid reservoir 36 can be fluidly connected to fluid flow channel 40 using a luer or locking luer arrangement. Luer and locking luer devices are well known in the relevant art. Alternatively, fluid reservoir 36 can be an integral part of filling tool 32.

Filling tool 32 further includes cannula 44 and plunger 46. Plunger 46 is mounted and constructed to be reciprocable within cannula 44, as depicted in FIG. 2, so as to force plug 34 outwardly through cannula 44 and into filling lumen 16. Plunger 46 can have a variety of configurations. Plunger 46 preferably is constructed of a relatively rigid plastic or metal material. The size and configuration of cannula 44 are selected such that cannula 44 can be fluidly connected to filling lumen 16 of feeding tube 12. In the preferred embodiment of the present invention, cannula 44 is configured to provide a substantially fluid-tight connection with filling lumen 16 when cannula 44 is inserted therein, thereby preventing leakage during the filling of retaining member 30. Due to the relative flexibility of feeding tube 12 and, in particular, filling lumen 16, it will be appreciated that cannula 44 can have an outer diameter that is substantially equal to or slightly greater than the inner diameter of filling lumen 16 and still be insertable into filling lumen 16. In this way, plug 34 inserted through cannula 44 can have the capacity to substantially fluidly seal filling lumen 16 when inserted therein. One or more apertures 42 are formed through the cannula at its first end portion 52 in order to provide fluid communication between fluid flow channel 40 and the interior of cannula 44.

A sealing member 48 is provided within filling tool 32. Sealing member 48 preferably is constructed of a material such as silicone. Sealing member 48 defines channel 50 therethrough. Channel 50 is positioned to be substantially coaxial to cannula 44, thereby facilitating passage of plug 32 through channel 50 and through cannula 44. Channel 50 and plunger 46 are constructed such that plunger 46 is reciprocable through channel 50. Channel 50 also is constructed to receive plug 34 therein. In the preferred embodiment of the present invention, sealing member 48 and plug 34 substantially fluidly isolate plunger 46 from cannula 44 and fluid flow channel 40 when plug 34 is in the position depicted in FIG. 2. Further, plunger 46 preferably is configured such that it substantially prevents the backflow of fluid through channel 50 as plug 34 is being urged through cannula 44, thereby substantially preventing leakage from filling tool 32.

Plunger 46 can be configured to be operable from an end of filling tool 32 remote from cannula 44. However, in the preferred embodiment depicted in FIG. 2, plunger 46 includes activator portion 56 which extends through slot 54 formed through filling tool 32, thereby enabling an operator to activate plunger 46 from a position above filling tool 32. Due to the travel of plunger 46 required to insert plug 34 into filling lumen 16, this orientation of activator portion 52 is believed to provide greater control of filling tool 32.

In the preferred embodiment of filling tool 32 of the present invention depicted in FIG. 2, alignment member 62 is provided on filling tool 32 to facilitate alignment of cannula 44 with filling lumen 16. Alignment member 62 is preferably configured for insertion into feeding lumen 14 of feeding tube 12. In the alternative, alignment member 62 can be configured to support an exterior surface of feeding tube 12, thereby facilitating insertion of cannula 44 into filling lumen 16.

The preferred embodiment of the present invention further includes one or more ribs 58 which extend from leading wall 60 of filling tool 32 to sealing member 48. Ribs 58 prevent forward motion of sealing member 48 relative to filling tool 32 as plunger 46 is moved to insert plug 34 into filling lumen 16, thereby ensuring that sealing member 48 prevents substantial fluid leakage from filling tool 32 during use. In the preferred embodiment, ribs 58 extend toward sealing member 48 from leading wall 60 a distance equal to or less than cannula 44 extends from leading wall 60 toward sealing member 48. Ribs 58 thereby restrain the forward motion of sealing member 48 as plunger 46 is moved to insert plug 34 into filling lumen 16.

The present invention is further directed to a method of placing and retaining a gastrostomy or jejunostomy tube in a patient. The method of the preferred embodiment of the present invention includes the step of providing a feeding tube constructed in accordance with feeding tube 12 described herein. Feeding tube 12 includes fillable retaining member 30 mounted on internal end portion 20 thereof. Feeding tube 12 defines feeding lumen 14 therethrough from external end portion 18 to internal end portion 20. Feeding tube 12 also defines filling lumen 16 therethrough where filling lumen 16 extends at least from a position on the internal end portion side of retaining member 30 to a position 31 on the external end portion side of retaining member 30, and where filling lumen 16 is in fluid communication with the interior of retaining member 30.

The method further includes the step of providing a tool for filling retaining member 30. For example, a tool for filling constructed in accordance with filling tool 32 of the present invention can be provided.

In the first embodiment of the method of the present invention, filling lumen 16 is open to an external environment at internal end portion 20 of feeding tube 12. In addition, filling lumen 16 is substantially fluidly sealed at or terminates at point 31. Retaining member 30 is filled by forcing fluid into filling lumen 16 at internal end portion 20 of feeding tube 12. In the preferred embodiment of the method of the present invention, filling tool 32 is used to fill retaining member 30 by inserting cannula 44 into filling lumen 16 at internal end portion 20. This step is facilitated by aligning alignment member 62 with feeding lumen 14 of feeding tube 12 at the same time cannula 44 is inserted into filling lumen 16. Filling of retaining member 30 in accordance with this embodiment of the present invention is preferably performed prior to introduction of apparatus tube 10 into the patient.

Following the filling of retaining member 30, filling lumen 16 is substantially fluidly sealed on the internal end portion side of retaining member 30. Sealing of filling lumen 16 can be achieved using a variety of known techniques such as heat sealing, the placement of an adhesive in filling lumen 16, or the placement of a plug in filling lumen 16. In the preferred embodiment of the method of the present invention, filling tool 32 is used to insert plug 34 into filling lumen 16 in order to seal fluidly filling lumen 16, thereby maintaining retaining member 30 in a filled condition. It will be appreciated that filling tool 32 of the present invention allows filling lumen 16 to be sealed after the filling of retaining member 30 without the need to remove filling tool 32 from feeding tube 12.

Feeding tube 12 next is placed in the patient such that retaining member 30 is positioned within the patient's stomach and such that external end portion 18 of feeding tube 12 is external to the patient. Point 31 is preferably positioned outside of the patient's body. It will be appreciated that feeding tube 12 can be placed in the patient using any known technique.

In order to empty retaining member 30, filling lumen 16 is severed or punctured at point 31 or at a point on the internal end portion side of point 31 such that fluid can escape therefrom. In order to facilitate deflation of retaining member 30, feeding tube 12 can be urged outwardly from the patient in order to apply pressure to retaining member 30. Following emptying of retaining member 30, apparatus 10 can be withdrawn from the patient's body through the stoma tract formed by the patient's body about feeding tube 12. During withdrawal of feeding tube 12 from the patient, retaining member 30 will collapse and lie against the exterior of feeding tube portion 12.

It will be appreciated that external end portion 18 of feeding tube 12 can be cut to any desired length without emptying retaining member 30, provided that the cut is made on the exterior end portion side of point 31. This feature of feeding tube 12 allows a medical professional to cut away external terminal end 24 of feeding tube 12 when it becomes worn and insert an adapter into the newly exposed terminal end of feeding tube 12 without emptying and re-filling retaining member 30 and without removing apparatus 10 from the patient. In addition, this feature of the present invention allows the medical professional to adjust the length of external end portion 24 of feeding tube 12 without emptying and re-filling retaining member 30 and without removing apparatus 10 from the patient.

In a second embodiment of the method of the present invention, a feeding tube 12 defining a feeding lumen 14 and a filling lumen 16 therethrough is provided. Feeding tube 12 has a fillable retaining member 30 mounted on an internal end portion 20 thereof. Filling lumen 16 extends from retaining member 30 to external end portion 18 of feeding tube 12 and is open to an external environment of feeding tube 12 through an aperture defined through external end portion 18, e.g., at external terminal end 24. Feeding tube 12 utilized in this embodiment of the present invention is depicted in FIG. 4. In this embodiment, filling lumen 16 is in fluid communication with the interior of retaining member 30. Filling lumen may extend from retaining member 30 to a point on the interior end portion side of retaining member 30. In the event that filling lumen 16 is open to an external environment of feeding tube 12 at a point on the interior end portion side of retaining member 30, filling lumen 16 must be fluidly sealed on the interior end portion side of retaining member 30 prior to placement of feeding tube 12 is placed in a patient such that retaining member 30 is positioned within the patient's stomach and such that external end portion 18 is external to the patient.

In the second embodiment of the method of the present invention, the retaining member is filled by forcing fluid through filling lumen 16 from a point on the external end portion side of retaining member 30. Filling of retaining member 30 can be performed prior to or subsequent to introduction of the feeding tube apparatus into the patient in this embodiment of the method of the present invention. In one configuration of the second embodiment of the present invention, filling tool 32 constructed in accordance with the disclosure set forth herein is provided and is used to fill retaining member 30 from distal end portion 18 of feeding tube 12.

Following the filling of retaining member 30, filling lumen 16 is substantially fluidly sealed. In one configuration of the second embodiment of the present invention, filling tool 32 is used to insert plug 34 into filling lumen 16 such that plug 34 is spaced from external terminal end 24 of feeding tube 12. However, as above-discussed with respect to the preferred embodiment of the method of the present invention, filling lumen 16 can be substantially fluidly sealed by other methods, including heat sealing and the placement of a body of adhesive therein.

Although the apparatus and method of the present invention have been described herein with respect to certain preferred embodiments, it will be appreciated by one of ordinary skill in the art that various modifications can be made to the present invention. Such modifications are intended to be within the scope of the appended claims.

What is claimed is:

1. A method for placing an enteral feeding tube, said method comprising the steps of:
    supplying a feeding tube having an internal end portion and an external end portion, said feeding tube defining a filling lumen and a feeding lumen therethrough, a fillable retaining member mounted on said internal end portion of said feed tube, said fillable retaining member in fluid communication with said filling lumen;
    providing a filling tool including a fluid reservoir containing a fluid, a tool body defining a fluid flow path fluidly connected to said fluid reservoir, a cannula constructed to connect fluidly to said filling lumen of said feeding tube, said cannula fluidly connected to said fluid flow path defined by said tool body, a plunger mounted for movement through said cannula, and a plug constructed to substantially fluidly seal the filling lumen of the feeding tube, said plug positioned within said filling tool so as to be displaced outwardly through said cannula when said plunger is moved towards said cannula;
    fluidly connecting said cannula to said filling lumen of said feeding tube;
    discharging fluid from said fluid reservoir to said fillable retaining member through said fluid flow path, said cannula, and said filling lumen;
    moving said plunger towards said cannula to displace the plug outwardly from the cannula and insert said plug into substantially sealing engagement with said filling lumen of said feeding tube; and
    positioning the feeding tube percutaneously in the gastrointestinal tract of a patient with the retaining member positioned internal to the patient and the external end portion positioned external to the patient.

2. The method of claim 1, wherein the cannula is fluidly connected to the filling lumen proximate the internal end portion of the feeding tube during the fluidly connecting step.

3. The method of claim 1, wherein the cannula is fluidly connected to the filling lumen proximate the external end portion of the feeding tube during the fluidly connecting step.

4. The method of claim 1, wherein the positioning step is performed prior to the step of discharging fluid from the fluid reservoir to the fillable retaining member.

5. The method of claim 1, wherein the positioning step is performed subsequent to the step of discharging fluid from the fluid reservoir to the fillable retaining member.

6. The method of claim 1 further including the step of cutting the external end portion of the feeding tube to a desired length extending externally from the patient.

* * * * *